United States Patent [19]

Desai et al.

[11] Patent Number: 5,558,876
[45] Date of Patent: Sep. 24, 1996

[54] TOPICAL OPHTHALMIC ACIDIC DRUG FORMULATIONS

[75] Inventors: Suketu Desai; Rajan Bawa, both of Fort Worth, Tex.

[73] Assignee: Alcon Laboratories, Inc., Fort Worth, Tex.

[21] Appl. No.: 412,435

[22] Filed: Mar. 29, 1995

[51] Int. Cl.$^6$ ...................................... A61K 9/10
[52] U.S. Cl. .................... 424/427; 424/422; 514/887; 514/914
[58] Field of Search ................... 424/422, 40 A, 424/427; 514/887, 914

[56] References Cited

U.S. PATENT DOCUMENTS

| | | | |
|---|---|---|---|
| 4,234,601 | 11/1980 | Gardocki | 514/567 |
| 4,237,140 | 12/1980 | Dudzinski | 514/282 |
| 4,269,835 | 5/1981 | Whittle | 514/357 |
| 4,322,427 | 3/1982 | Buyniski et al. | 514/289 |
| 4,559,343 | 12/1985 | Han et al. | 514/264 |
| 4,587,249 | 5/1986 | Sunshine et al. | 514/265 |
| 4,656,177 | 4/1987 | Sunshine et al. | 514/264 |
| 4,777,174 | 10/1988 | Sunshine et al. | 514/264 |
| 4,960,799 | 10/1990 | Nagy | 514/567 |
| 5,110,493 | 5/1992 | Cherng-Chyi et al. | 514/413 |

FOREIGN PATENT DOCUMENTS

0621036A1  10/1994  European Pat. Off. .
94/15597   7/1994   WIPO .

OTHER PUBLICATIONS

Is mail, *Chemical Abstracts*, vol. 122, 1994, #170242.
Product Inserts from Physicians' Desk Reference for: Acular®, Voltaren™, Ocufen®, and Profenal®.

*Primary Examiner*—Thurman K. Page
*Assistant Examiner*—P. Webber
*Attorney, Agent, or Firm*—Sally Yeager

[57] ABSTRACT

Stable, comfortable, preserved, topical, ophthalmic compositions of acidic drugs are disclosed. Methods for their use are also disclosed.

12 Claims, 1 Drawing Sheet

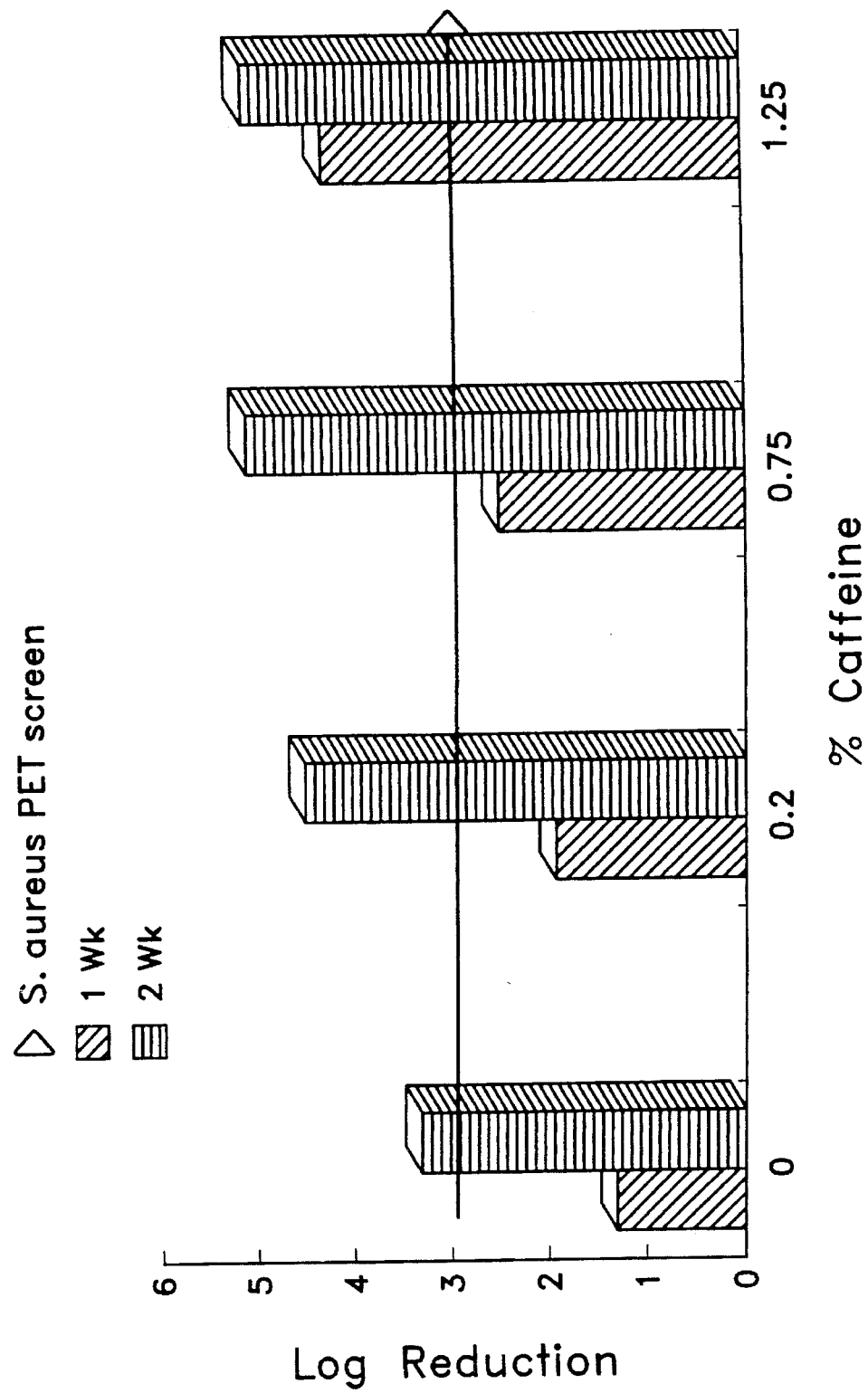

5,558,876

TOPICAL OPHTHALMIC ACIDIC DRUG FORMULATIONS

FIELD OF THE INVENTION

This application is directed to stable and comfortable preserved ophthalmic formulations containing an acidic drug.

BACKGROUND OF THE INVENTION

Carboxyl containing compounds, including most non-steroidal antiinflammatory drugs (NSAIDs), are difficult to formulate into stable, preserved, comfortable, ophthalmic compositions. Acidic drugs with carboxyl groups are inherently irritating to the eye. In addition, the drugs tend to form insoluble complexes with quaternary ammonium preservatives, such as benzalkonium chloride (BAC). Many NSAIDs have been formulated with other than desirable preservatives (e.g. sorbic acid, thimerosol) because the compounds complex with desired preservatives, such as, quaternary ammonium compounds, particularly BAC. In addition, it has proved difficult to formulate carboxyl containing compounds that are comfortable when applied topically to the eye.

There are ophthalmic products containing acidic drugs. Commonly, these drugs are NSAIDs containing a carboxyl group. Examples of these products are suprofen (Profenal®, Alcon Laboratories, Inc. which is preserved with thimerosol); diclofenac sodium (Voltaren Ophthalmic™, Ciba Vision Ophthalmics which is preserved with sorbic acid); flurbiprofen sodium (Ocufen®, Allergan Medical Optics which is preserved with thimerosol); and ketorolac tromethamine (Acular®, Allergan, Inc. which is preserved with BAC and Octoxynol 40).

U.S. Pat. No. 5,110,493 discloses aqueous, ophthalmic, non-steroidal anti-inflammatory formulations which include a preservative system formed of a quaternary ammonium compound and a nonionic surfactant which is an ethoxylated alkyl phenol, such as Octoxynol 10 or 40.

WO 94/15597 discloses the use of lauralkonium chloride, a $C_{12}$ homologue of BAC, which is compatible with acidic drug entities in ophthalmic formulations.

U.S. Pat. No. 4,960,799 discloses an ophthalmic formulation of a salt of ortho-(2,6-dichlorophenyl) aminophenylacetic acid, EDTA, a solubilizer, and a bacteriostat.

EP 0,621,036-A1 discloses ophthalmic formulations of particular arginine amides and either cyclodextrin or caffeine. The application discloses that the use of cyclodextrin or caffeine improves the arginine amide solubility in water and that the caffeine can stabilize the compound in water.

U.S. Pat. No. 4,559,343 discloses ophthalmic formulations containing NSAIDs and a xanthine derivative to reduce ocular discomfort.

The compositions of the present invention are stable, yet they contain an acidic drug and the desired preservative, BAC, or mixtures of at least two homologues of BAC. In addition, the compositions are comfortable upon topical instillation in the eye.

SUMMARY OF THE INVENTION

The present invention is directed to stable, comfortable, and preserved topical ophthalmic formulations comprising an acidic drug, Vitamin E Tocopherol Polyethylene Glycol 1000 Succinate (TPGS) (Eastman Chemical Co., Kingsport, Tenn., BAC, or mixtures of at least two homologues of BAC, and caffeine. Types of acidic drugs can include NSAIDs, antibacterials, diagnostic agents, antiinfective agents, and prostaglandins. Methods for the compositions' use are also disclosed.

BRIEF DESCRIPTION OF THE DRAWING

FIG. 1 shows the effect of caffeine concentration on the preservative efficacy of BAC.

DETAILED DESCRIPTION OF PREFERRED EMBODIMENTS

The compositions of the present invention comprise an acidic drug, Vitamin E TPGS, BAC, or mixtures of BAC homologues, such as $C_{12}$ and $C_{14}$ and caffeine. As used herein the term "acidic" means the drug contains a carboxyl moiety or a salt thereof and/or a sulfamide group or a salt thereof.

Acidic drugs which can be formulated according to the present invention include NSAIDs, including, but not limited to, diclofenac, bromfenac, fiurbiprofen, naproxen, ketorolac, suprofen, ibuprofen, and tolmetin, including their pharmaceutically acceptable salts, esters, and prodrugs; prostaglandins; antibacterial and antiinfective agents; and diagnostic agents. BAC is used to preserve the formulations. The Vitamin E TPGS is used to solubilize the acidic drug and reduce ocular discomfort in aqueous conditions. The caffeine is added to reduce ocular discomfort, but surprisingly, it was found that it acts synergistically with Vitamin E TPGS to reduce discomfort and it also potentiates the preservative efficacy of BAC.

In the formulations, the acidic drug is present at concentrations from 0.001 weight percent (wt. %) to 2.5 wt. %, preferably 0.01 to 1.0 wt. %. The Vitamin E TPGS concentration is 0.0001 to 30 wt. %, preferably 0.01 to 10 wt. %. BAC or its homologue mixtures are present at concentrations from 0.00001 to 0.02 wt. %, preferably 0.0001 to 0.01 wt. %; and the caffeine concentration is from 0.001 to 5.0 wt. %, preferably 0.01 to 1.0 wt. %.

The compositions of the invention may also contain other components such as, but not limited to, those listed below:

1. Buffers (e.g., phosphate, borate, citrate, acetate, carbonate, borate-polyol complexes, etc.);

2. Tonicity agents (e.g. mannitol, sodium chloride, xylitol, etc.)

3. Viscosity building agents, e.g., carboxylic polymers like Carbopol® (carbomers), Noveon® (polycarbophils), etc.; cellulose derivatives including alkyl and hydroxyalkyl cellulose like methylcellulose, hydroxypropylcellulose, carboxymethylcellulose, etc.; gums like locust beam, xanthan, agarose, karaya, guar, etc.; and other polymers including but not limited to polyvinyl alcohol, polyvinyl pyrollidone, polyethylene glycol, Pluronic® (Poloxamers), tragacanth, and hyaluronic acid.

4. Phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. The phase-transition in these polymers can be mediated by changes in environmental factors such as ionic strength, pH, or temperature alone or in combination with other factors.

5. Other excipients include but are not limited to: antioxidants (ascorbic acid, sodium metabisulfite, etc.), complexing agents (cyclodextrins and derivatives thereof), drug carriers or drug-laden ion exchange carriers, such as, Amberlite® and Duolite®, and some chelating agents.

The ophthalmic compositions can be administered topically to the eye as suspensions, emulsions, ointments, gels, or solutions. The compositions may be aqueous or nonaqueous, but are preferably aqueous. The compositions may have the drugs incorporated and/or encapsulated in microcapsules, nanocapsules, nanoparticles, or liposomes which are dispersed in an aqueous or nonaqueous medium.

The preferred formulation of this invention comprises diclofenac sodium, as illustrated in Example 2.

The following Examples are illustrative, but not limiting:

Examples 1 and 2 are useful in treating ophthalmic inflammation. The formulations are administered 1–4 times daily according to the routine discretion of a skilled clinician.

EXAMPLE 1

| Ingredients | Concentration (% wt./vol.) |
| --- | --- |
| NSAID | 0.1–2.5 |
| HPMC | 0.05–1.0 |
| Tromethamine | 0.1–1.2 |
| Boric Acid | 0.01–1.0 |
| Vit E TPGS | 0.1–5.0 |
| Caffeine | 0.01–2.0 |
| Mannitol | 2.0–4.4 |
| Benzalkonium Chloride or its homologue mixtures | 0.005–0.01 |
| Disodium EDTA | 0.01–0.1 |
| HCl/NaOH | q.s. to pH 7.4 |
| Purified Water | q.s. 100% |

Compounding Procedure:

To a tared glass vessel containing purified water, first caffeine is added. The solution is stirred until the caffeine dissolves. Next, the rest of the ingredients are added in the order given below and each ingredient is completely dissolved by stirring before the next one is added.

NSAID

Vitamin E TPGS

Tromethamine

Boric acid

Disodium EDTA

Benzalkonium chloride

Mannitol

HPMC

The formulation is then brought to 95% of its final weight. The pH is adjusted to about 7–7.4 using NaOH or HCl. The final weight is adjusted to 100% with purified water. The formulation's tonicity is 300 mOsms.

| Ingredients | Concentration (% w/w) |
| --- | --- |
| Diclofenac Sodium | 0.1 |
| HPMC | 0.1 |
| Tromethamine | 1.2 |
| Boric Acid | 0.6 |
| Vit E TPGS | 2.0 |
| Caffeine | 0.2 |
| Mannitol | 4.2 |
| Benzalkonium Chloride | 0.01 |

-continued

| Ingredients | Concentration (% w/w) |
| --- | --- |
| Disodium EDTA | 0.1 |
| HCl/NaOH | q.s. pH 7.4 |
| Purified Water | q.s. 100% |

Compounding Procedure:

A. Preparing 10% Vitamin E TPGS stock solution

Deionized water (70% of final weight of TPGS stock solution) was taken in a large beaker and brought to boiling with heat. The required quantity of Vitamin E TPGS was added in small proportions under stirring. Final weight was adjusted to 100% with additional d.i. water after all of Vitamin E TPGS had gone in solution.

B. Preparing 2% HPMC (Hydroxypropyl methyl cellulose) stock solution

HPMC wad added in small proportions under constant stirring into a beaker containing deionized water which was 70% of final weight of HPMC stock solution. Final weight was adjusted to 100% with additional d.i. water after all of the added FIPMC had dissolved completely.

C. Ingredients were added in the order suggested below and each ingredient was dissolved completely under constant stirring before the next one was added:

0.2 g of caffeine was weighed in a tared vessel containing a stir bar and d.i. water which is 40% of final weight. Then 0.1 g of diclofenac, 20 g of 10% Vitamin E TPGS stock solution, 1.2 g of tromethamine, 0.6 g of boric acid, 0.1 g of disodium EDTA, 0.01 g of BAC, 4.2 g of mannitol and 5 g of 2% HPMC stock solution were added sequentially. Weight was adjusted to 95% of final weight with d.i. water. Next, pH was measured and if necessary, it was adjusted to 7.4 with 0.1N NaOH or 0.1N HCl. Finally weight was adjusted to 100 g with additional d.i. water.

Example 3

Examples of other NSAID and prostaglandin formulations

| Formulation | % weight by volume | | | | | |
| --- | --- | --- | --- | --- | --- | --- |
| Ingredient | A | B | C | D | E | F |
| Caffeine | 0.2 | 0.2 | 0.2 | 0.2 | 0.2 | 0.2 |
| Flurbiprofen | 0.03 | — | — | — | — | — |
| Bromfenac | — | 0.05 | — | — | — | — |
| Suprofen | — | — | 0.25 | — | — | — |
| Suprofen | — | — | — | 0.25 | — | — |
| Prostaglandin (PGE$_2$) | — | — | — | — | 0.1 | — |
| Prostaglandin (PGF$_{2\alpha}$) | — | — | — | — | — | 0.1 |
| 10% Vitamin E TPGS Stock Soln. | 20.0 | 20.0 | 15.0 | 20.0 | 25.0 | 25.0 |
| tromethamine | 1.0 | 1.0 | 1.2 | 1.2 | 1.0 | 1.0 |
| boric acid | 0.6 | 0.6 | 0.6 | 0.6 | 0.6 | 0.6 |
| Disodium EDTA | 0.05 | 0.05 | 0.05 | 0.05 | 0.05 | 0.05 |
| Benzalkonium Chloride (BAC) | 0.01 | 0.01 | — | 0.01 | 0.01 | — |
| C12 and C14 homologues of BAC (80:20) | — | — | 0.01 | — | — | 0.01 |
| Mannitol | 4.2 | 4.2 | 3.8 | 3.8 | 4.0 | 4.0 |
| 2% HPMC Stock Soln. | 15.0 | 15.0 | 15.0 | 15.0 | 15.0 | 15.0 |
| 0.1N NaOH or 0.1N HCl to adjust pH | 7.4 | 7.4 | 7.4 | 7.4 | 7.4 | 7.4 |
| Deionized water qs to | 100 | 100 | 100 | 100 | 100 | 100 |

Compounding Procedure:

Formulations A–F are prepared by adding caffeine to a tared glass vessel containing deionized water. The solution is stirred until caffeine is dissolved. Next, the remaining ingredients are added sequentially as listed and after the previous ingredient has completely dissolved. The solution is then brought to 95% of final weight with water and the pH is adjusted to 7.4. The final weight is then made 100% with water.

EXAMPLE 4

A simplified preservative efficacy screen based on the United States Pharmacopeia (USP) XXII, 1990 Antimicrobial Preservative Effectiveness standards was performed against Staphylococcus aureus for the compositions shown in the following table. The screen entailed challenging the formulations with the gram-positive bacteria, S. aureus, and sampling at 7 and 14 days. The initial preservative efficacy test for the formulations had indicated that the formulations had poor preservation only against S. aureus, whereas the formulations exhibited appropriate preservative efficacy according to USP against the other organisms such as gram-negative (Pseudomonas aeruginosa) and fungi (Aspergillus niger) at 7 and 14 days.

| Formulation Ingredient | A | B | C | D |
| --- | --- | --- | --- | --- |
| Caffeine | 0.0 | 0.2 | 0.75 | 1.25 |
| Diclofenac Sodium | 0.1 | 0.1 | 0.1 | 0.1 |
| Vitamin E TPGS | 1.5 | 1.5 | 1.5 | 1.5 |
| Tromethamine | 1.2 | 1.2 | 1.2 | 1.2 |
| Boric acid | 0.6 | 0.6 | 0.6 | 0.6 |
| Disodium EDTA | 0.1 | 0.1 | 0.1 | 0.1 |
| BAC | 0.01 | 0.01 | 0.01 | 0.01 |
| Mannitol | 4.4 | 4.4 | 3.8 | 3.2 |
| HPMC | 0.1 | 0.1 | 0.1 | 0.1 |
| NaOH or HCl, qs to adjust pH to | 7.4 | 7.4 | 7.4 | 7.4 |
| Purified Water, qs to | 100 | 100 | 100 | 100 |

According to the USP preservative efficacy standards for S. aureus, a formulation has to exhibit a minimum of 3.0 log reduction on day 14 and no increase in count between 14 to 28 days. FIG. 1 shows the results for the S. aureus screen for the formulations in the above table. The formulations had similar compositions except for the varying concentrations of caffeine from 0.0% to 1.25%. As shown in FIG. 1, the higher the caffeine concentration in the formulation the higher was the S. aureus log reduction value. The figure also shows that the required 3.0 log reduction is achieved by 7 days at higher caffeine concentration rather than on 14 days.

The formulation of Example 2 above showed the S. aureus log reduction values of 3.1 and 5.1 on days 7 and 14, respectively, when the S. aureus screen was performed.

Thus, surprisingly caffeine was found to potentiate the preservative efficacy of BAC in the formulations of the invention.

We claim:

1. A topical ophthalmic aqueous solution comprising an acidic drug, tocophersolan, benzalkonium chloride or mixtures of at least two homologues of benzalkonium chloride, and caffeine.

2. The composition of claim 1 having the following concentrations; 0.001 to 2.5 wt. % acidic drug; 0.0001 to 30 wt. % tocophersolan; 0.00001 to 0.02 wt. % benzalkonium chloride; and 0.001 to 5.0 wt. % caffeine, 3. The composition of claim 2 wherein the acidic drug is selected from the group consisting of a non-steroidal anti-inflammatory drug and a prostaglandin.

4. The composition of claim 3 wherein the acidic drug is a non-steroidal anti-inflammatory drug.

5. The composition of claim 4 wherein the non-steroidal anti-inflammatory drug is selected from the group consisting of diclofenac, bromfenac, flurbiprofen, naproxen, ketorolac, suprofen, ibuprofen, and tolmetin and their salts and esters.

6. The composition of claim 5 wherein the non-steroidal anti-inflammatory drug is diclofenac.

7. A topical ophthalmic composition comprising 0.01 to 2.5 wt. % non-steroidal anti-inflammatory drug, 0.0001 to 30 wt. % tocophersolan, 0.00001 to 0.02 wt. % benzalkonium chloride or mixtures of at least two homologues of benzalkonium chloride, and 0.001 to 5.0 wt. % caffeine.

8. The composition of claim 7 wherein the non-steroidal anti-inflammatory drug is selected from the group consisting of diclofenac, bromfenac, flurbiprofen, naproxen, ketorolac, suprofen, ibuprofen, and tolmetin and their salts and esters.

9. The composition of claim 8 wherein the non-steroidal anti-inflammatory drug is diclofenac.

10. A method for treating inflammation of the eye, which comprises, applying the composition of claim 7 to the inflamed eye.

11. The method of claim 10 wherein the non-steroidal anti-inflammatory drug is diclofenac.

12. A method for treating an eye with an acidic drug, which comprises, applying the composition of claim 1 to the eye.

* * * * *